US008270699B2

(12) United States Patent
Rodrigues et al.

(10) Patent No.: US 8,270,699 B2
(45) Date of Patent: Sep. 18, 2012

(54) METHOD FOR MEASURING COATING APPEARANCE AND THE USE THEREOF

(75) Inventors: Allan Blase Joseph Rodrigues, Bloomfield Hills, MI (US); Arun Prakash, West Chester, PA (US); Judith Elaine Obetz, Newtown Square, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 491 days.

(21) Appl. No.: 12/443,292

(22) PCT Filed: Oct. 2, 2007

(86) PCT No.: PCT/US2007/021196
§ 371 (c)(1),
(2), (4) Date: Mar. 27, 2009

(87) PCT Pub. No.: WO2008/042394
PCT Pub. Date: Apr. 10, 2008

(65) Prior Publication Data
US 2010/0027870 A1 Feb. 4, 2010

Related U.S. Application Data

(60) Provisional application No. 60/848,676, filed on Oct. 2, 2006.

(51) Int. Cl.
*G06K 9/00* (2006.01)

(52) U.S. Cl. ............ 382/141; 356/445; 356/237.3
(58) Field of Classification Search ............ 356/445, 356/448, 237.1–241.6; 382/141–167
See application file for complete search history.

(56) References Cited

U.S. PATENT DOCUMENTS

| 4,731,856 | A  | * | 3/1988  | Lloyd et al. ............ 382/141 |
|-----------|----|---|---------|----------------------------------|
| 5,054,101 | A  | * | 10/1991 | Prakash ................. 382/270 |
| 5,249,029 | A  | * | 9/1993  | Sommer et al. ......... 356/336   |
| 5,602,646 | A  | * | 2/1997  | Bernardin et al. ....... 356/445  |
| 6,278,482 | B1 | * | 8/2001  | Ashizaki ................ 348/86  |
| 6,952,265 | B2 |   | 10/2005 | Prakash et al.                   |
| 6,975,404 | B2 |   | 12/2005 | Schwarz                          |
| 7,782,490 | B2 | * | 8/2010  | Mestha et al. .......... 358/1.9  |
| 7,859,675 | B2 | * | 12/2010 | Maryfield et al. ....... 356/445  |
| 2004/0218182 | A1 | * | 11/2004 | Alman et al. ........... 356/402 |
| 2004/0252308 | A1 | * | 12/2004 | Prakash et al. .......... 356/445 |
| 2005/0123186 | A1 | * | 6/2005  | Reeves et al. ........... 382/141 |
| 2006/0039603 | A1 | * | 2/2006  | Koutsky ................. 382/165 |
| 2006/0251315 | A1 | * | 11/2006 | Okabe et al. ............ 382/141 |
| 2008/0235224 | A1 | * | 9/2008  | Rodrigues et al. ........ 707/6   |

* cited by examiner

*Primary Examiner* — Tarifur Chowdhury
*Assistant Examiner* — Michael P Lapage
(74) *Attorney, Agent, or Firm* — Gann G. Xu

(57) ABSTRACT

The present invention is directed to a method for obtaining appearance characteristics of a target coating containing effect pigments. The present invention is also directed to a method for comparing appearances of two or more coatings by comparing the appearance characteristics. The present invention is further directed to a system for obtaining appearance characteristics of one or more coatings and comparing said coating appearances.

18 Claims, 4 Drawing Sheets

METHOD FOR MEASURING COATING APPEARANCE AND THE USE THEREOF

FIELD OF INVENTION

The present invention is directed to a method for obtaining appearance characteristics of a target coating containing effect pigments. The present invention is also directed to a method for comparing appearances of two or more coatings by comparing the appearance characteristics. The present invention is further directed to a system for obtaining appearance characteristics of one or more coatings and comparing said coating appearances.

BACKGROUND OF INVENTION

Surface coatings containing effect pigments, such as light absorbing pigment, light scattering pigments, light interference pigments, and light reflecting pigments are well known. Metallic flake pigments, for example aluminum flakes, are examples of such effect pigments and are especially favored for the protection and decoration of automobile bodies, such as for example by reason of their imparting a differential light reflection effect, usually referred, to as "flop", as well as flake appearance effects, which include texture, sparkle, glint and glitter imparted by the flake as well as the enhancement of depth perception in the coating. The appearance effects are a function of the flake type, flake size distribution, surface smoothness, orientation, and uniformity of flake edges. Metallic coatings usually also contain pigments, generally of a light absorbing rather than a light scattering type. These light absorbing pigments interact with effect pigments such as flakes to change the appearance effect of the coating. In general, visual coating appearance includes texture, sparkle, glitter or other visual effects of a coating. The visual appearance can vary when viewed from varying viewing angles, with varying illumination angles, or with varying illumination intensities.

Traditionally, coating appearance is measured based on human eye judgment. Some attempts were made to measure appearance of a target coating using instruments. U.S. Pat. No. 6,952,265, disclosed a method to obtain appearance data of a target coating in digital images and correlate the appearance data to appearance characteristics stored in a coating database. However, it requires to: (1) obtain images of the target coating at multiple illumination intensities and (2) measure the images at the multiple illumination intensities and at multiple threshold levels. U.S. Pat. No. 6,975,404 disclosed a process and device for measuring appearance properties of a coating having reflective flakes. However, it requires measurement at multiple illumination angles.

It is therefore still in need for a simple method and system for measuring and comparing coating appearances that are without the need for measuring appearance at multiple illumination intensities and angles and substantially independent from human visual judgment.

STATEMENT OF INVENTION

This invention is directed to a method for obtaining appearance characteristics of a target coating containing effect pigments, said method comprising the steps of:
 a) providing illuminations to the target coating at a fixed illumination angle and at varying illumination intensities;
 b) selecting an effective illumination intensity under which the effect pigments of the target coating exhibit varying brightness;
 c) capturing at least one image of the target coating under the effective illumination intensity using an imaging device;
 d) identifying from the image by a computing device, appearance features comprising a set of bright features from bright areas of said image where the effect pigments exhibit highest brightness, a set of intermediate features from intermediate areas of the image where the effect pigments exhibit intermediate brightness, and a set of dark features from dark areas of the image where the target coating is essentially free of detectable said effect pigments;
 e) generating individual feature values based on the appearance features; and
 f) generating the appearance characteristics based on the individual feature values.

This invention is also directed to a method for comparing appearances of an alternate coating containing alternate effect pigments to a target coating containing target effect pigments, said method comprising the steps of:
 a) providing illuminations to the target coating or the alternate coating at a fixed illumination angle and at varying illumination intensities;
 b) selecting an effective illumination intensity under which at least one of the target coating or the alternate coating having effect pigments exhibit varying brightness;
 c) capturing at least one target image of the target coating and at least one alternate image of the alternate coating under the effective illumination intensity using an imaging device;
 d) identifying by a computing device, target features from the target image and alternate features of the alternate image,
  wherein the target features comprise a set of target bright features from bright areas of said target image where the target effect pigments exhibit highest brightness, a set of target intermediate features from intermediate areas of the target image where the target effect pigments exhibit intermediate brightness, and a set of target dark features from dark areas of the target image where the target coating is essentially free of detectable said target effect pigments; and
  wherein the alternate features comprise a set of alternate bright features from bright areas of said alternate image where the alternate effect pigments exhibit highest brightness, a set of alternate intermediate features from intermediate areas of the alternate image where the alternate effect pigments exhibit intermediate brightness, and a set of alternate dark features from dark areas of the alternate image where the alternate coating is essentially free of detectable said alternate effect pigments;
 e) generating individual target feature values based on the target features and individual alternate feature values based on the alternate features;
 f) generating target appearance characteristics based on the individual target feature values and alternate appearance characteristics based on the individual alternate feature values; and
 g) comparing appearances of the alternate coating and the target coating by comparing the alternate appearance characteristics and the target appearance characteristics.

This invention is directed to a system for generating appearance characteristics of a target coating containing effect pigments, said system comprising:
 a) means for providing illuminations to the target coated at a fixed illumination angle and at varying illumination intensities;
 b) means for selecting an effective illumination intensity under which the effect pigments of the target coating exhibit varying brightness;
 c) an imaging device for capturing at least one target image of the target coating under the effective illumination intensity;
 d) a computing device comprising a display member, a memory member, and a processor; and
 e) a computer program product residing in the memory member causing the computing device to perform a computing process comprising the steps of:
  i) receiving the image from the imaging device;
  ii) identifying from the target image by the computing device, appearance features comprising a set of bright features from bright areas of said image where the effect pigments exhibit highest brightness, a set of intermediate features from intermediate areas of the image where the effect pigments exhibit intermediate brightness, and a set of dark features from dark areas of the image where the target coating is essentially free of detectable said effect pigments;
  iii) generating individual feature values based on the appearance features; and
  iv) generating the appearance characteristics based on the individual feature values.

This invention is further directed to a system for comparing appearances of an alternate coating containing alternate effect pigments to a target coating containing target effect pigments, said system comprising:
 a) means for providing illuminations to the target coating or the alternate coating at a fixed illumination angle and at varying illumination intensities;
 b) means for selecting an effective illumination intensity under which at least one of the target coating or the alternate coating having effect pigments exhibit varying brightness;
 c) an imaging device for capturing at least one target image of the target coating and at least one alternate image of the alternate coating under the effective illumination intensity;
 d) a computing device comprising a display member, a memory member, and a processor;
 e) a computer program product residing in the memory member causing the computing device to perform a computing process comprising the steps of:
  i) receiving the target image and the alternate image from the imaging device;
  ii) identifying target features from the target image and alternate features of the alternate image,
   wherein the target features comprise a set of target bright features from bright areas of said target image where the target effect pigments exhibit highest brightness, a set of target intermediate features from intermediate areas of the target image where the target effect pigments exhibit intermediate brightness, and a set of target dark features from dark areas of the target image where the target coating is essentially free of detectable said target effect pigments; and
   wherein the alternate features comprise a set of alternate bright features from bright areas of said alternate image where the alternate effect pigments exhibit highest brightness, a set of alternate intermediate features from intermediate areas of the alternate image where the alternate effect pigments exhibit intermediate brightness, and a set of alternate dark features from dark areas of the alternate image where the alternate coating is essentially free of detectable said alternate effect pigments;
  iii) generating individual target feature values based on the target features and individual alternate feature values based on the alternate features;
  iv) generating target appearance characteristics based on the individual target feature values and alternate appearance characteristics based on the individual alternate feature values; and
  v) comparing appearances of the alternate coating and the target coating by comparing the alternate appearance characteristics and the target appearance characteristics.

DETAILED DESCRIPTION OF PREFERRED EMBODIMENT

Figure 1:
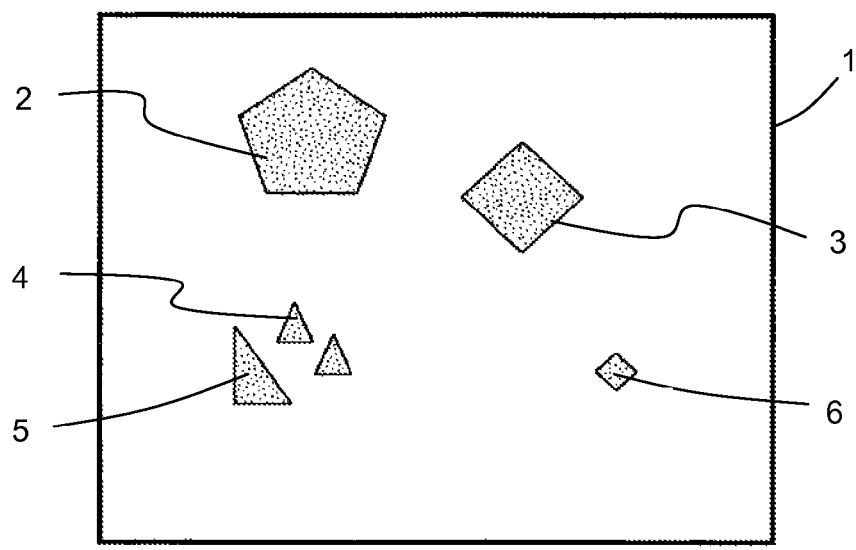
FIG. 1 is a schematic representation of bright features detectable above a first threshold level T1.

The aspects and advantages of the present invention will be more readily understood, by those of ordinary skill in the art, from reading the following detailed description. It is to be appreciated that certain aspects of the invention, which are, for clarity, described above and below in the context of separate embodiments, may also be provided in combination in a single embodiment. Conversely, various aspects of the invention that are, for brevity, described in the context of a single embodiment, may also be provided separately or in any subcombination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

As used herein:

The term "pigment" or "pigments" used herein refers to a colorant or colorants that produce color or colors. A pigment can be from natural and synthetic sources and made of organic or inorganic constituents. A pigment also includes metallic particles or flakes with specific or mixed shapes and dimensions. A pigment is usually not soluble in a coating composition.

The term "effect pigment" or "effect pigments" refers to pigments that produce special effects in a coating. Examples of effect pigments include, but not limited to, light absorbing pigment, light scattering pigments, light interference pigments, and light reflecting pigments are well known. Metallic flakes, for example aluminum flakes, are also examples of such effect pigments.

"Appearance" used herein refers to (1) the aspect of visual experience by which a coating is viewed or recognized; and (2) perception in which the spectral and geometric aspects of a coating is integrated with its illuminating and viewing environment. In general, appearance includes texture, sparkle, glitter, or other visual effects of a coating. Appearance usually varies with varying viewing angles or varying illumination angles.

Gonioapparent flakes refer to flakes pertaining to change in appearance with change in illumination angle or viewing angle. Metallic flakes, such as aluminum flakes are examples of gonioapparent flakes.

The term "dye" means a colorant or colorants that produce color or colors. Dye is usually soluble in a coating composition.

The term "database" refers to a collection of related information that can be searched and retrieved. The database can be a searchable electronic numerical or textual document, a searchable PDF document, an Microsoft Excel® spreadsheet, an Microsoft Access® database (both supplied by Microsoft Corporation of Redmond, Wash.), an Oracle® database (supplied by Oracle Corporation of Redwood Shores, Calif.), or a Lynux database, each registered under their respective trademarks. The database can be a set of electronic documents, photographs, images, diagrams, or drawings, residing in a computer readable storage media that can be searched and retrieved. A database can be a single database or a set of related databases or a group of unrelated databases. "Related database" means that there is at least one common information element in the related databases that can be used to relate such databases. One example of the related databases can be Oracle® relational databases.

The term "vehicle", "automotive", "automobile", "automotive vehicle", or "automobile vehicle" refers to an automobile such as car, van, mini van, bus, SUV (sports utility vehicle); truck; semi truck; tractor; motorcycle; trailer; ATV (all terrain vehicle); pickup truck; heavy duty mover, such as, bulldozer, mobile crane and earth mover; airplanes; boats; ships; and other modes of transport that are coated with coating compositions.

A computing device used herein refers to a data processing chip, a desktop computer, a laptop computer, a pocket PC, a personal digital assistant (PDA), a handheld electronic processing device, a smart phone that combines the functionality of a PDA and a mobile phone, or any other electronic devices that can process information automatically. A computing device can be built into other electronic devices, such as a built-in data processing chip integrated into an imaging device. A computing device may have a wired or wireless connection to a database or to another computing device. A computing device may be a client computer that communicates with a host computer in a multi-computer client-host system connected via a wired or wireless network including intranet and internet. A computing device can also be configured to be coupled with a data input or output device via wired or wireless connections. For example, a laptop computer can be operatively configured to receive color data and images through a wireless connection. A "portable computing device" includes a laptop computer, a pocket PC, a personal digital assistant (PDA), a handheld electronic processing device, a mobile phone, a smart phone that combines the functionality of a PDA and a mobile phone, a tablet computer, or any other electronic devices that can process information and data and can be carried by a person.

Wired connections include hardware couplings, splitters, connectors, cables or wires. Wireless connections and devices include, but not limited to, Wi-Fi device, Bluetooth device, wide area network (WAN) wireless device, local area network (LAN) device, infrared communication device, optical data transfer device, radio transmitter and optionally receiver, wireless phone, wireless phone adaptor card, or any other devices that can transmit signals in a wide range of radio frequency including visible or invisible optical wavelengths and electromagnetic wavelengths.

An imaging device refers to a device that can capture images under a wide range of radio frequency including visible or invisible optical wavelengths and electromagnetic wavelengths. Examples of the imaging device include, but not limited to, a still film optical camera, an X-Ray camera, an infrared camera, and a video camera. A digital imager or digital imaging device refers to an imaging device captures images in digital signals. Examples of the digital imager include, but not limited to, a digital still camera, a digital video camera, a digital scanner, and a charge couple device (CCD) camera. An imaging device can capture images in black and white, gray scale, or various color levels. A digital imager is preferred in this invention. Images captured using a non-digital imaging device, such as a still photograph, can be converted into digital images using a digital scanner and can be also suitable for this invention.

This invention is directed to a method for obtaining appearance characteristics of one or more coatings and comparing appearances of one or more coatings by comparing said appearance characteristics.

Appearance characteristics can be generated using methods described in the following embodiments. In brief, the appearance characteristics can be obtained by capturing one or more target images using an imaging device and subsequent measurement of the target images using a computing device. The target images can be still images or video images. Both still images and video images are suitable for this invention. The target images, either still or video images can be stored in digital formats for measurement of appearance characteristics at same time or at a later time. The target images can also be captured and transmitted to a computing device for measurement of appearance without being stored permanently, such as real-time video images without being stored. In this invention, stored images are preferred, and stored still images are further preferred. In another embodiment, appearance data are generated by an appearance measurement device and stored as non-image electronic files. Examples of such non-image electronic files include, but not limited to, textual, numerical or alphanumerical data files correlating positions and reflectance intensity at each of the positions. Image and non-image data files can be converted to each other according to well known methods. For example, an image can be measured using methods described below and stored into separate appearance data files.

In one embodiment, appearance characteristics of a target coating containing flakes are obtained with a method described below.

In step a), illuminations at a fixed illumination angle and at varying illumination intensities is directed to the target coating. The fixed illumination angle can be at a perpendicular (0°), also known as normal (0°) angle to the surface of target coating, or an angle within the range from −5° to +5° from the normal. Illumination intensity is in such a range that sparkles caused by the flakes are brighter than other target coating areas where no flakes are visible. The flakes in the target coating exhibit varying brightness or sparkles under the varying illumination intensities.

In step b), illumination intensity setting is selected so that the brightest parts of the image are at or close to a maximum image intensity level while at the same time objects at lower image intensities are still visible in the image. A commonly used imaging device stores digital images with image intensity levels ranging from 0 to 255 wherein 0 represents the darkest and 255 represents brightest parts of an image. When such commonly used imaging device is used, the maximum image intensity level is 255. This range comes from the 8 bits data format used to represent the data of any one pixel in the digital image. When other data formats are used, image intensity levels may change. Those skilled in the art can select any workable data formats, image intensities and illumination intensities without departing from the spirit and scope of this invention. The selected illumination intensity is referred to as an effective illumination intensity.

In step c), at least one image of the target coating under the effective illumination intensity is captured using the aforementioned imaging device. An imaging device refers to a device that can capture images under a wide range of electromagnetic wavelengths including visible or invisible wavelengths. Preferred imaging device is a digital still camera, a digital video camera, a digital scanner, or a charge couple device (CCD) camera. An imaging device can capture images in black and white, gray scale, or various color levels.

The image captured by the imaging device can be stored in one of the commonly used digital image file formats, such as, but not limited to .bmp (Windows Bitmap) .tif or .tiff (Tagged Image File Format), .jpg or .jpeg (Joint Photographic Experts Group image file format), .gif (Graphics Interchange Format), or .wmf (Windows Metafile format). The images can also be captured in analog format and converted into digital format by methods well known to those skilled in the art. The images can even be analog or digital video images. The images can be entered into a computing device through a wired or wireless connection.

In step d), the image is measured by the computing device to identify appearance features. An appearance feature is a characteristic or attribute that contributes to the visual appearance of a coating. An appearance feature can be identified and localized as a sparkle object, a flake or a flake-like object, a physical distance between two adjacent objects, a region where one or more objects reside, a region having multiple objects, or a combination thereof. A feature can also be characteristic or attribute such as distribution of intensities, variation of intensities, or other statistical descriptions of the coating appearance. Appearance features can be quantitative or qualitative descriptions of the appearance of the coating. Quantitative descriptions, such as size, brightness, or other descriptions with numeric values are preferred. In a preferred embodiment, appearance features can comprise a set of bright features from bright areas of said image where the effect pigments such as metallic flakes exhibit highest brightness, a set of intermediate features from intermediate areas of the image where the effect pigments exhibit intermediate brightness, and a set of dark features from dark areas of the image where the target coating is essentially free of detectable said effect pigments.

Figure 2:
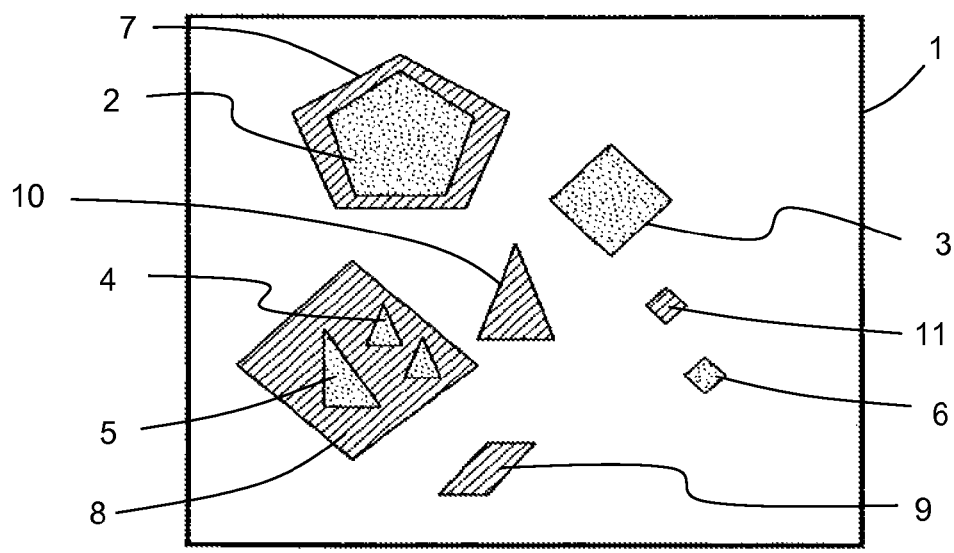
FIG. 2 is a schematic representation of bright and intermediate features detectable above a second threshold level T2.
Figure 3:
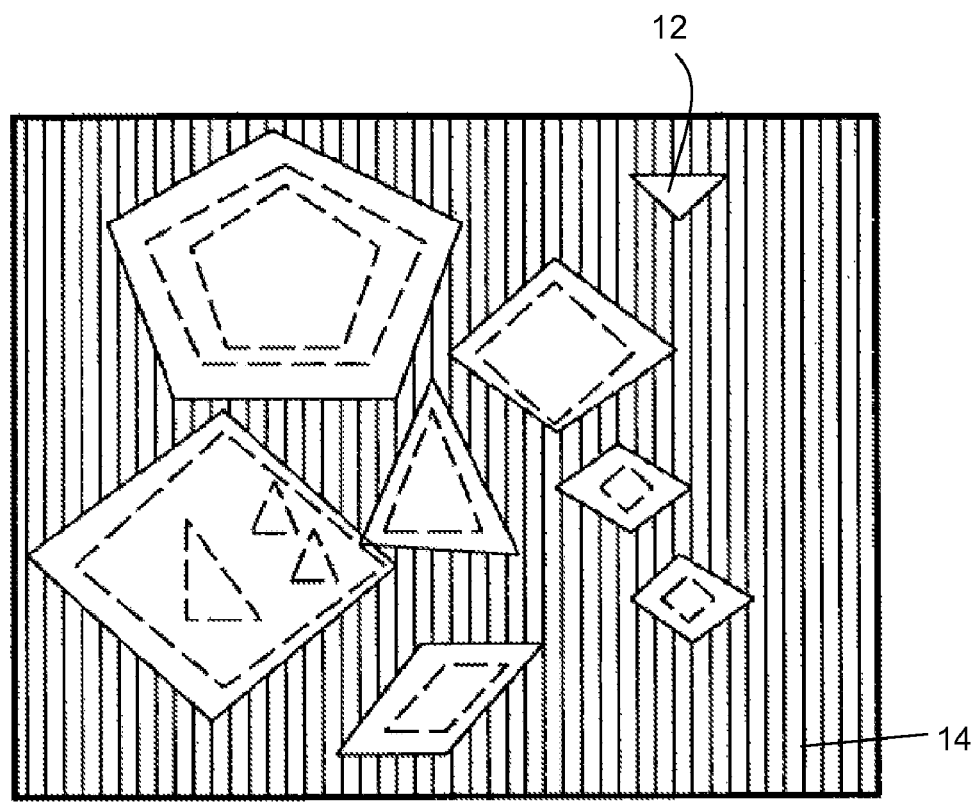
FIG. 3 is a schematic representation of features detectable above a third threshold level T3. The crosshatched area represents dark features having image intensity below the threshold levels T3. Dotted lines represent boundaries of features detectable above T1 or T2 threshold levels.

Measurement can be done by setting different threshold levels wherein a threshold level used herein refers to an image intensity level where any pixels having image intensity level equal or greater than the threshold level will be measured. For example, a threshold level T1 of 225 can be set for bright areas meaning that pixels or regions of pixels of the image having image intensity equal or greater than 225 will be identified as bright features, such as objects 2-6 in the area 1 of FIG. 1 or object 15 in FIG. 5A. A second threshold level T2 can be set at 150 for intermediate brightness. Objects having image intensity equal or greater than 150 can be identified as intermediate features, such as objects 7-11 in FIG. 2 or objects 16 and 17 in FIG. 5B. A threshold level T3 of 100 can be set for dark features meaning that pixels or regions of pixels of the image having image intensity below 100 will be identified as dark features, such as area 14 in FIG. 3 or area 18 in FIG. 5C where essentially no flakes or flake-like objects are detectable. Some other objects, such as objects 12 and 13 in FIG. 3 or object 19 in FIG. 5C that have image intensities below the threshold level T2, but above T3 can be identified and considered when generating dark feature values.

In step e), individual feature values are generated for individual appearance features identified. A number of feature values can be generated based on features identified. Examples of feature values include: (1) Total number of distinct and contiguous sparkle objects having image intensity equal or greater than a set first threshold level T1; (2) Average number of small sparkle objects measured in each of the images; (3) Average number of medium sparkle objects measured in each of the images; (4) Average number of large sparkle objects measured in each of the images; (5) Average number of extra large sparkle objects measured in each of the images; (6) Fractional area of each image having image intensities above the set first threshold level (Area T1); (7) The number of sparkle objects where the size of the sparkle object is expanded at a second Threshold Level T2, such as objects 7 and 8 in FIG. 2; (8) Average number of new sparkle objects wherein a new sparkle object is a contiguous area that is distinct at the second Threshold Level T2, such as objects 9, 10 and 11 in FIG. 2; (9) Fractional area of each image having image intensities greater than the second threshold level T2; (10) Fractional area of each image having sparkle objects expanded at the second Threshold Level T2 comparing to that at the first Threshold Level T1 (Area Exp); (11) Fractional area of each image having new sparkle objects at the second Threshold Level T2 (Area New); and (12) Fractional area of each image having image intensities below a third threshold level T3, such as the area 14 in FIG. 3. Additional features can be identified and additional feature values may be generated as determined necessary by those skilled in the art. Examples of such additional features include objects 12 and 13 in FIG. 3 that have image intensity between T2 and T3.

In step f), appearance characteristics are generated based on the individual feature values generated in step e). Examples of such appearance characteristics include such ratios of Area Exp/Area T1 and Area New/Area T1. These ratios are related to physical properties of flakes in the coating and contribute to the appearance of the target coating. Other appearance characteristics may be generated as determined necessary by those skilled in the art.

This invention is also directed to a method comparing appearances of one or more alternate coatings containing alternate effect pigments to a target coating containing target effect pigments. The alternate effect pigments and the target effect pigments can be the same or different pigments. Said method generates target appearance characteristics of the target coating and a plurality of alternate appearance characteristics of the one or more alternate coatings using the same steps a)-f) as described above. The plurality of appearance characteristics are then compared to that of the target coating based on selected algorithms. An example of such an algorithm is described below.

First, individual ratio of feature values Area Exp/Area T1 and Area New/Area T1 are calculated for the target coating and each of the alternate coatings using the equations below.

$R_{EA}$=Area Exp/Area $T1$ $R_{NA}$=Area New/Area $T1$.

Then, individual feature distance between the ratio of feature values of the target coating and each of the alternate coatings can be calculated and a root mean square (RMS) of the feature distances can be obtained using the equation below:

$$RMS=(((R_{EA\text{-}Alt}-R_{EA\text{-}Tgt})^2+(R_{NA\text{-}Alt}-R_{NA\text{-}Tgt})^2)/2)^{1/2}$$

Wherein:
$R_{EA\text{-}Alt}$ is an $R_{EA}$ value of an alternate coating;
$R_{EA\text{-}Tgt}$ is the $R_{EA}$ value of the target coating;
$R_{NA\text{-}Alt}$ is an $R_{EN}$ value of an alternate coating;
$R_{NA\text{-}Tgt}$ is an $R_{EN}$ value of the target coating.

Based on calculation results of the feature distances, each of the alternate coatings can be ranked based on its closeness in appearance compared to the target coating. The alternate coating with the smallest RMS is the one with the closest appearance compared to the target coating.

It is to be noted that only two ratios are used in the example described above. Additional features, feature values, or feature distances can be used as determined necessary by those skilled in the art. It is also understood that different weighing factors may be given to one or more features, feature values or feature distances to generate weighed sum of feature distances. Examples of weighing factors and calculations for weighed feature distances are described in detail in aforementioned U.S. Pat. No. 6,952,265.

Appearance characteristics can be generated without capturing target images. It can be done by detecting the reflectance of the target coating and directly recording in a non-image data file such as a set of histograms files, binary data files, or other non-image data files that can record appearance information. Any aforementioned digital imaging devices can be configured directly or through a converter to generate non-image data file, such as a binary data file. An image recorded by an analog imaging device such as a photograph captured by a still film camera, can be converted into a digital image, or a non-image data file by, for example, a scanner. Those who are skilled in the art can use the methods described above or variations thereof to generate appearance characteristics based on the non-image data files.

This invention is further directed to a system for generating appearance characteristics of a target coating containing effect pigments.

One embodiment of such system comprises: a) means for providing illuminations to the target coated at a fixed illumination angle and at varying illumination intensities; b) means for selecting an effective illumination intensity under which the effect pigments of the target coating exhibit varying brightness; c) an imaging device for capturing at least one target image of the target coating under the effective illumination intensity; d) a computing device comprising a display member, a memory member, and a processor; and e) a computer program product residing in the memory member for performing a computing process to i) receive the target image from the imaging device; ii) identify from the target image, appearance features comprising a set of bright features from bright areas of said image where the effect pigments exhibit highest brightness, a set of intermediate features from intermediate areas of the image where the effect pigments exhibit intermediate brightness, and a set of dark features from dark areas of the image where the target coating is essentially free of detectable said effect pigments; iii) generate individual feature values based on the appearance features; and iv) generate the appearance characteristics based on the individual feature values.

The means for providing illuminations typically include a light source, such as, the IT3900 with a tungsten-halogen lamp EKE supplied by Illumination Technologies Inc., East Syracuse, N.Y. and a fiber optic bundle A08025.60 supplied by Schott Fostec Inc., Auburn, N.Y. that is capable of producing beams of illumination in the visible light range of from 400 nanometers to 700 nanometers at set intensities. The system, which is preferably portable, is preferably provided with an enclosed extension to house the light source. However, applicants also contemplate using alternative means, such as the MHF-C50LR light source with an LM-50 lamp and a fiber optic bundle connected to a MML4-45D micro machine lens system, supplied by Moritex USA Inc., San Jose, Calif. to pipe-in the illumination beams from the light source. The means for selecting an effective illumination intensity can be any conventional means, such as a voltage regulator that can change the current to the filament of the light source. The illumination intensity can be controlled in accordance with a conventional software program run from a computer to achieve the preset intensities. The computer used here to control the illumination intensity can be the same aforementioned computing device for receiving the image or a separate computer or a separate computer. Any suitable computer can be used, such as, for example, Dell Precision M50 model supplied by Dell Computer Corp., Round Rock, Tex. If desired, the system may comprise additional means such as a collimating lens or an aperture, for collimating the one or more beams of light emanating from light source as determined necessary by those skilled in the art. The imaging means is preferably a digital imager such as a digital still camera, a digital video camera, a digital scanner, or a charge couple device (CCD) camera.

This invention is even further directed to a system for comparing appearances of an alternate coating containing alternate effect pigments to a target coating containing target effect pigments. The system generates target appearance characteristics and alternate appearance characteristics according to the methods and by the means described above. The target and the alternate appearance characteristics are then compared according to the algorithm described before.

The methods and the systems of this invention can be used for measuring appearances of original automotive coatings (OEM coatings) and for matching the OEM coatings in repair and refinish of such OEM coatings.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Measurement of Appearance

Figure 4:
FIG. 4 shows a representative coating image in gray scale.

A target image was captured using an imaging device TM-7EX from Jai Pulnix of San Jose, Calif., USA. Illumination angle was set at 0° normal to the surface of the target coating and an effective illumination intensity was selected so flakes in the target coating show varying brightness. The imaging device stores digital images with image intensity levels ranging from 0 to 255. This range comes from the 8 bits data format used to represent the data of any one pixel in the digital image. The effective illumination intensity setting is selected so that the brightest parts of the image are at or close to image intensity level 255 while at the same time objects at lower image intensities are still visible in the image. Images of alternate coatings were captured using the same effective illumination intensity. A representative target coating image in gray scale is shown in FIG. 4.

Three different threshold levels were set for measuring appearance characteristics from captured images: T1 being the highest, T2 being the intermediate and T3 representing the background. A threshold level used herein refers to an image intensity level where any pixels having image intensity level equal or greater than the threshold level will be measured. For the measurement described in this example, following threshold levels were set as:

T1=225,
T2=150, and
T3=100.

The following features were then extracted from each of the images using a computer program product. For each image, pixels of entire image were measured. For statistical purposes, more than one image can be measured. Some data shown in the example represent average values of the measurements from more than one image. The images were captured at the same or different portions of the target or alternate coatings. Some features have a size associated with them. The size or size range is described below. Based on predetermined sizes described below, features were categorized into different categories, such as small, medium, large and extra large. It is understood that those skilled in the art may choose different sizes for some or all the features as determined appropriate for a coating under measurement.

1) At Threshold Level T1:

No. of Object: Total number of distinct and contiguous sparkle objects with image intensity equal or greater than the T1 threshold.

No. of Sm: Average number of small sparkle objects measured in each of the portions of each of the images. A small sparkle object is defined as an object having the size smaller than 10-20 micrometers. Objects smaller than 10 micrometers were ignored in this particular measurement.

No. of Med: Average number of medium sparkle objects measured in each of the portions of each of the images. A medium sparkle object is defined as an object having the size of 20-30 micrometers.

Figure 5A:
FIG. 5 shows the coating image at 3 different threshold levels. A: image showing bright features of different sizes above threshold level T1; B: same image above the threshold level T2; and C: same image at the threshold level T3.

No. of Lg: Average number of large sparkle objects measured in each of the portions of each of the images. A large sparkle object is defined as an object having the size of 30-50 micrometers. Object 15 in FIG. 5A is an example of such large object (bright feature large).

No. of ExLg: Average number of extra large sparkle objects measured in each of the portions of each of the images. An extra large sparkle object is defined as an object having the size larger than 50 micrometers.

Area T1: Fractional area of the image having image intensities above the threshold level T1. An average value was given for each coating based on measurements of multiple images of that coating.

Measurement data are shown in Table 1. A representative image is shown in FIG. 5A. The bright areas are sparkle objects having image intensity equal or greater than threshold level T1.

TABLE 1

Measurement Data at T1 Threshold Level.

| Coatings | No. of Objects | No. of Sm | No. of Med | No. of Lg | No. of ExLg | Area T1 |
| --- | --- | --- | --- | --- | --- | --- |
| Target | 226 | 37.4 | 45.6 | 15.2 | 4.4 | 0.5 |
| Alt A | 229 | 44.6 | 37.2 | 16.8 | 10.8 | 0.57 |
| Alt B | 131 | 23 | 20.2 | 9.2 | 4.6 | 0.3 |
| Alt C | 126 | 24.8 | 21.8 | 2.8 | 0.8 | 0.18 |
| Alt D | 313 | 68.4 | 51.8 | 9.2 | 2.2 | 0.5 |
| Alt E | 66 | 15.2 | 8 | 3.2 | 1.6 | 0.12 |
| Alt F | 287 | 56.8 | 43 | 19 | 6.4 | 0.59 |
| Alt G | 108 | 18 | 16.4 | 6.2 | 2.4 | 0.29 |

2) At Threshold Level T2:

No. of Exp: Average number of sparkle objects in the four aforementioned categories, namely small, medium, large and extra large as described above, where the size of the sparkle object is expanded at the Threshold Level T2 comparing to at the Threshold Level T1. An example of expanded area is the object 16 in FIG. 5B. The dotted line 15a represents the boundary of the same sparkle object detectable at the threshold level T1. An average value was given for each coating based on measurements of multiple images of that coating (Table 2).

Figure 5B:
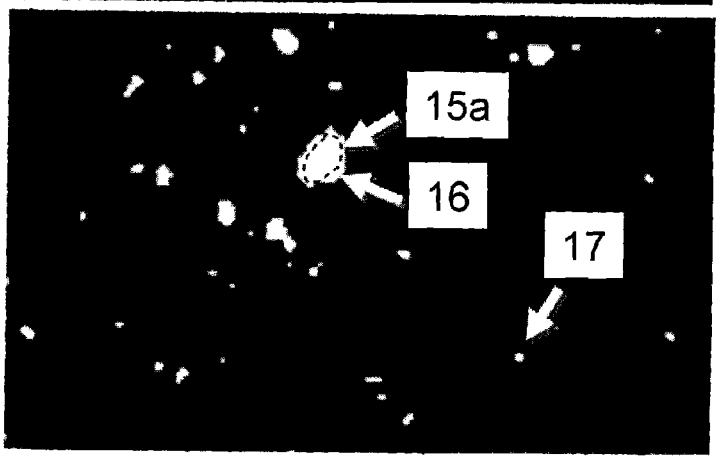

No. of New: Average number of new sparkle objects in the four aforementioned categories wherein a new sparkle object is a contiguous area that is distinct from any sparkle objects detected at the Threshold Level T1. The sparkle object 17 in FIG. 5B is an example of such new sparkle objects. An average value was given for each coating based on measurements of multiple images of that coating (Table 2).

Area Exp: Fractional area of the image having sparkle objects expanded at the Threshold Level T2 comparing to that at the Threshold Level T1. An average value was given for each coating based on measurements of multiple images of that coating (Table 3).

Area New: Fractional area of the image having new sparkle objects at the Threshold Level T2. An average value was given for each coating based on measurements of multiple images of that coating (Table 3).

Area Hi: A sum of Area Exp and Are New described above. An average value was given for each coating based on measurements of multiple images of that coating (Table 3).

Figure 5C:
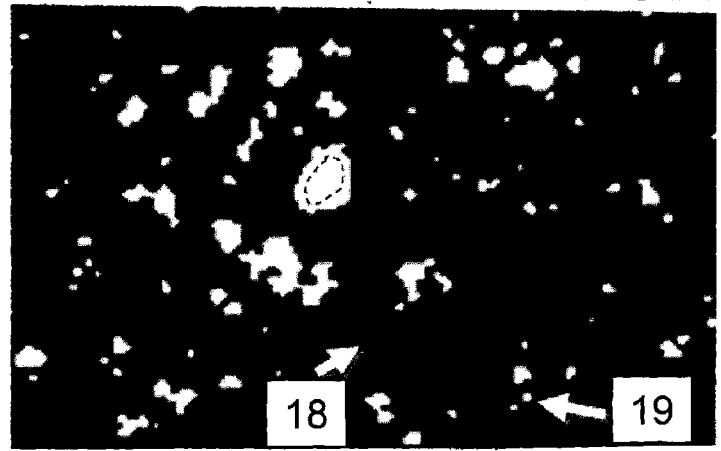

3) At Threshold Level T3:

Area Mid: Fractional area of the image having image intensities between the threshold levels T2 and T3. An average value was given for each coating based on measurements of multiple images of that coating. Area 19 in FIG. 5C is an example of such area having image intensity between T2 and T3: the object was not detectable at T2, but detectable at T3.

Area Lo: Fractional area of the image having image intensities below the threshold level T3. An average value was given for each coating based on measurements of multiple images of that coating. The crosshatched area 14 in FIG. 3 and the dark area 18 in FIG. 5C are examples of such Area Lo.

TABLE 2

Feature Values at T2 Threshold Level.

| Coatings | No. of Expanded Objects at T2 Threshold Level | | | | No. of New Objects at T2 Threshold Level | | | | |
|---|---|---|---|---|---|---|---|---|---|
| | No. of Sm | No. of Med | No. of Lg | No. of ExLg | No. of Objects | No. of Sm | No. of Med | No. of Lg | No. of ExLg |
| Target | 0.2 | 65.4 | 68.2 | 39.6 | 693 | 127 | 57.2 | 6.4 | 0.4 |
| Alt A | 0.2 | 62 | 56.6 | 49.8 | 773 | 128 | 76.8 | 7.4 | 0 |
| Alt B | 0.2 | 30.6 | 39.2 | 29.8 | 588 | 107 | 65 | 7.8 | 1.6 |
| Alt C | 0.2 | 45.8 | 34.4 | 12.2 | 638 | 127 | 66.6 | 7.8 | 0.8 |
| Alt D | 0.6 | 98.8 | 81.2 | 46.8 | 1236 | 230 | 137 | 12 | 1.8 |
| Alt E | 0.2 | 20 | 16.2 | 14.6 | 446 | 86.4 | 50 | 6.2 | 0.2 |
| Alt F | 0 | 92.4 | 73.4 | 53.4 | 1000 | 195 | 92 | 5 | 0.2 |
| Alt G | 0 | 18.6 | 32.6 | 30.2 | 595 | 111 | 71.4 | 13.4 | 3 |

TABLE 3

Feature Values at T2 and T3 Threshold Levels.

| Coatings | Area Exp | Area New | Area Hi | Area Mid | Area Lo |
|---|---|---|---|---|---|
| Target | 1.44 | 0.62 | 2.1 | 62.3 | 35.6 |
| Alt A | 1.61 | 0.74 | 2.3 | 61.3 | 36.3 |
| Alt B | 0.96 | 0.64 | 1.6 | 63.2 | 35.2 |
| Alt C | 0.67 | 0.67 | 1.3 | 62.3 | 36.3 |
| Alt D | 1.83 | 1.28 | 3.1 | 61.7 | 35.2 |
| Alt E | 0.44 | 0.5 | 0.9 | 64.5 | 34.6 |
| Alt F | 1.81 | 0.9 | 2.7 | 60.6 | 36.7 |
| Alt G | 0.85 | 0.73 | 1.6 | 66.3 | 32.1 |

TABLE 4

RMS of Feature Distances.

| Coatings | Area Exp/ Area T1 | Area New/ Area T1 | RMS of Feature Distance from the Target Coating |
|---|---|---|---|
| Target | 2.88 | 1.24 | — |
| Alt A | 2.82 | 1.30 | 0.06 |
| Alt B | 3.20 | 2.13 | 0.67 |
| Alt C | 3.72 | 3.72 | 1.85 |
| Alt D | 3.66 | 2.56 | 1.08 |
| Alt E | 3.67 | 4.17 | 2.14 |
| Alt F | 3.07 | 1.53 | 0.24 |
| Alt G | 2.93 | 2.52 | 0.90 |

Comparison of Appearance Data

Appearance features of the target coating were compared to the appearance features of the alternate coatings by calculating and comparing corresponding feature values. The calculation and comparison were performed by a computer program product based on principles and considerations described below.

First, individual ratio of feature values Area Exp/Area T1 and Area New/Area T1 were calculated using the equations below.

$$R_{EA} = \text{Area Exp/Area } T1$$

$$R_{NA} = \text{Area New/Area } T1$$

Wherein corresponding feature values Area T1 are shown in Table 1, and Area Exp and Area New are shown in Table 3.

Then, individual feature distances $R_{EA\text{-}Alt} - R_{EA\text{-}Tgt}$, $R_{NA\text{-}Alt} - R_{NA\text{-}Tgt}$ and a root mean square (RMS) of the feature distances were calculated using the equation below:

$$\text{RMS} = (((R_{EA\text{-}Alt} - R_{EA\text{-}Tgt})^2 + (R_{NA\text{-}Alt} - R_{NA\text{-}Tgt})^2)/2)^{1/2}$$

Wherein:
- $R_{EA\text{-}Alt}$ is an $R_{EA}$ value of an alternate coating;
- $R_{EA\text{-}Tgt}$ is the $R_{EA}$ value of the target coating;
- $R_{NA\text{-}Alt}$ is an $R_{EN}$ value of an alternate coating;
- $R_{NA\text{-}Tgt}$ is an $R_{EN}$ value of the target coating.

Calculation results of the feature distances are shown in Table 4.

Based on RMS results shown in Table 4, the following initial appearance ranking for the alternate coatings was generated (Table 5).

TABLE 5

Initial Appearance Ranking.

| Alternate Coatings | Initial Appearance Ranking |
|---|---|
| Alt A | 1 |
| Alt F | 2 |
| Alt B | 3 |
| Alt G | 4 |
| Alt D | 5 |
| Alt C | 6 |
| Alt E | 7 |

Additional feature values were then considered for top ranked alternate coatings. Differences of the numbers of extra large sparkle objects (No. of ExLg column in Table 1) were compared. Based on the data in Table 1, it was determined that the highest ranked Alt A coating has too many extra large sparkle objects that may result in a coarser coating compared to the target coating. The alternate coating Alt F was then moved up in ranking list. This process was repeated for the top 3 alternate coatings in generating a refined appearance ranking: Alt F was the best match in appearance, Alt B and Alt A were also satisfactory for matching appearance of the target coating within acceptable tolerance. Final appearance comparison results are shown in Table 6.

TABLE 6

Results on Appearance Comparison.

| Alternate Coatings | Initial Appearance Ranking | Refined Appearance Ranking | Match Appearance | Comments |
|---|---|---|---|---|
| Target | — | — | — | — |
| Alt F | 2 | 1 | Yes | Best Match |
| Alt A | 1 | 2 | Yes | 2$^{nd}$ Choice |
| Alt B | 3 | 3 | Yes | 2$^{nd}$ Choice |
| Alt G | 4 | — | No | |
| Alt D | 5 | — | No | |
| Alt C | 6 | — | No | |
| Alt E | 7 | — | No | |

What is claimed is:

1. A method for obtaining appearance characteristics of a target coating containing effect pigments, said method comprising the steps of:
 a) providing illuminations to the target coating at a fixed illumination angle and at varying illumination intensities;
 b) selecting an effective illumination intensity under which the effect pigments of the target coating exhibit varying brightness;
 c) capturing at least one image of the target coating under the effective illumination intensity using an imaging device;
 d) identifying from the image by a computing device, appearance features comprising a set of bright features from bright areas of said image where the effect pigments exhibit highest brightness with pixels having image intensity level equal to or greater than a first threshold level, a set of intermediate features from intermediate areas of the image where the effect pigments exhibit intermediate brightness with pixels having image intensity level equal to or greater than a second threshold level, and a set of dark features from dark areas of the image having image intensity below a third threshold level where the target coating is essentially free of detectable said effect pigments, wherein all pixels or regions of pixels of the image having image intensity below said third threshold level are identified as the dark features;
 e) generating individual feature values based on the appearance features, wherein said individual feature values comprise fractional areas of the image having image intensities above said first threshold level based on said set of bright features, fractional areas of the image having image intensities at said second threshold level based on said set of intermediate features, and fractional areas of the image having image intensities below said third threshold level based on said set of dark features; and
 f) generating the appearance characteristics based on the individual feature values.

2. The method of claim 1, wherein the effect pigments are gonioapparent flakes.

3. The method of claim 1, wherein the target coating is affixed to surface of an automotive body.

4. The method of claim 1, wherein the imaging device is a digital imager.

5. A method for comparing appearances of an alternate coating containing alternate effect pigments to a target coating containing target effect pigments, said method comprising the steps of:
 a) providing illuminations to the target coating or the alternate coating at a fixed illumination angle and at varying illumination intensities;
 b) selecting an effective illumination intensity under which at least one of the target coating or the alternate coating having effect pigments exhibit varying brightness;
 c) capturing at least one target image of the target coating and at least one alternate image of the alternate coating under the effective illumination intensity using an imaging device;
 d) identifying by a computing device, target features from the target image and alternate features of the alternate image,
  wherein the target features comprise a set of target bright features from bright areas of said target image where the target effect pigments exhibit highest brightness with pixels having image intensity level equal to or greater than a first threshold level, a set of target intermediate features from intermediate areas of the target image where the target effect pigments exhibit intermediate brightness with pixels having image intensity level equal to or greater than a second threshold level, and a set of target dark features having fractional or a from dark areas of the target image having image intensity below a third threshold level where the target coating is essentially free of detectable said target effect pigments, wherein all pixels or regions of pixels of the target image having image intensity below said third threshold level are identified as the target dark features; and
  wherein the alternate features comprise a set of alternate bright features from bright areas of said alternate image where the alternate effect pigments exhibit highest brightness with pixels having image intensity level equal to or greater than the first threshold level, a set of alternate intermediate features from intermediate areas of the alternate image where the alternate effect pigments exhibit intermediate brightness with pixels having image intensity level equal to or greater than the second threshold level, and a set of alternate dark features from dark areas of the alternate image having image intensity below the third threshold level where the alternate coating is essentially free of detectable said alternate effect pigments, wherein all pixels or regions of pixels of the alternate image having image intensity below said third threshold level are identified as the alternate dark features; and
 e) generating individual target feature values based on the target features and individual alternate feature values based on the alternate features, wherein said individual target feature values comprise fractional areas of the target image having image intensities above said first threshold level based on said set of target bright features, fractional areas of the target image having image intensities at said second threshold level based on said set of target intermediate features, and fractional areas of the target image having image intensities below said third threshold level based on said set of target dark features;
  wherein said individual alternate feature values comprise fractional areas of the alternate image having image intensities above said first threshold level based on said set of alternate bright features, fractional areas of the alternate image having image intensities at said second threshold level based on said set of alternate intermediate features, and fractional areas of the alternate image having image intensities below said third threshold level based on said set of alternate dark features;

f) generating target appearance characteristics based on the individual target feature values and alternate appearance characteristics based on the individual alternate feature values; and g) comparing appearances of the alternate coating and the target coating by comparing the alternate appearance characteristics and the target appearance characteristics.

6. The method of claim 5, wherein the effect pigments are gonioapparent flakes.

7. The method of claim 5, wherein the target coating is affixed to surface of an automotive body.

8. The method of claim 5, wherein the imaging device is a digital imager.

9. A system for generating appearance characteristics of a target coating containing effect pigments, said system comprising:
  a) means for providing illuminations to the target coating at a fixed illumination angle and at varying illumination intensities;
  b) means for selecting an effective illumination intensity under which the effect pigments of the target coating exhibit varying brightness;
  c) an imaging device for capturing at least one target image of the target coating under the effective illumination intensity;
  d) a computing device comprising a display member, a memory member, and a processor; and
  e) a computer program product residing in the memory member causing the computing device to perform a computing process comprising the steps of:
    i) receiving the target image from the imaging device;
    ii) identifying from the target image by the computing device, appearance features comprising a set of bright features from bright areas of said image where the effect pigments exhibit highest brightness with pixels having image intensity level equal to or greater than a first threshold level, a set of intermediate features from intermediate areas of the image where the effect pigments exhibit intermediate brightness with pixels having image intensity level equal to or greater than a second threshold level, and a set of dark features from dark areas of the image having image intensity below a third threshold level where the target coating is essentially free of detectable said effect pigments, wherein all pixels or regions of pixels of the image having image intensity below said third threshold level are identified as the dark features;
    iii) generating individual feature values based on the appearance features, wherein said individual feature values comprise fractional areas of the target image having image intensities above said first threshold level based on said set of bright features, fractional areas of the target image having image intensities at said second threshold level based on said set of intermediate features, and fractional areas of the target image having image intensities below said third threshold level based on said set of dark features; and
    iv) generating the appearance characteristics based on the individual feature values.

10. The system of claim 9, wherein the effect pigments are gonioapparent flakes.

11. The system of claim 9, wherein the target coating is affixed to surface of an automotive body.

12. The system of claim 9, wherein the imaging device is a digital imager.

13. A system for comparing appearances of an alternate coating containing alternate effect pigments to a target coating containing target effect pigments, said system comprising:
  a) means for providing illuminations to the target coating or the alternate coating at a fixed illumination angle and at varying illumination intensities;
  b) means for selecting an effective illumination intensity under which at least one of the target coating or the alternate coating having effect pigments exhibit varying brightness;
  c) an imaging device for capturing at least one target image of the target coating and at least one alternate image of the alternate coating under the effective illumination intensity;
  d) a computing device comprising a display member, a memory member, and a processor;
  e) a computer program product residing in the memory member causing the computing device to perform a computing process comprising the steps of:
    i) receiving the target image and the alternate image from the imaging device;
    ii) identifying target features from the target image and alternate features of the alternate image,
      wherein the target features comprise a set of target bright features from bright areas of said target image where the target effect pigments exhibit highest brightness with pixels having image intensity level equal to or greater than a first threshold level, a set of target intermediate features from intermediate areas of the target image where the target effect pigments exhibit intermediate brightness with pixels having image intensity level equal to or greater than a second threshold level, and a set of target dark features area from dark areas of the target image having image intensity below a third threshold level where the target coating is essentially free of detectable said target effect pigments, wherein all pixels or regions of pixels of the target image having image intensity below said third threshold level are identified as the target dark features; and
      wherein the alternate features comprise a set of alternate bright features from bright areas of said alternate image where the alternate effect pigments exhibit highest brightness with pixels having image intensity level equal to or greater than the first threshold level, a set of alternate intermediate features from intermediate areas of the alternate image where the alternate effect pigments exhibit intermediate brightness with pixels having image intensity level equal to or greater than the second threshold level, and a set of alternate dark features from dark areas of the alternate image having image intensity below the third threshold level where the alternate coating is essentially free of detectable said alternate effect pigments, wherein all pixels or regions of pixels of the alternate image having image intensity below said third threshold level are identified as the alternate dark features;
    iii) generating individual target feature values based on the target features and individual alternate feature values based on the alternate features, wherein said individual target feature values comprise fractional areas of the target image having image intensities above said first threshold level based on said set of target bright features, fractional areas of the target image having image intensities at said second threshold level based on said set of target intermediate features, and fractional areas of the target image having image intensities below said third threshold level based on said set of target dark features; wherein said individual alternate feature values comprise fractional areas of the alternate image having image intensities above said first threshold level based on said set of alternate bright features, fractional areas of the alternate image having image intensities at said second threshold level based on said set of alternate intermediate features, and fractional areas of the alternate image having image intensities below said third threshold level based on said set of alternate dark features;

iv) generating target appearance characteristics based on the individual target feature values and alternate appearance characteristics based on the individual alternate feature values; and v) comparing appearances of the alternate coating and the target coating by comparing the alternate appearance characteristics and the target appearance characteristics.

14. The system of claim 13, wherein the effect pigments are gonioapparent flakes.

15. The system of claim 13, wherein the target coating is affixed to surface of an automotive body.

16. The system of claim 13, wherein the imaging device is a digital imager.

17. The system of any one of claims 13-16 further comprising a database for storing and retrieving said features and appearance characteristics, wherein the database is accessible from the computing device.

18. The system of any one of claims 13-16, wherein the imaging device is operatively coupled to the computing device via wired or wireless connections.

* * * * *